United States Patent
Luo et al.

(10) Patent No.: US 12,352,163 B2
(45) Date of Patent: Jul. 8, 2025

(54) INTEGRATED TIME-LAPSE GAS GEOCHEMISTRY AND EQUATION OF STATE MODELING FOR EVALUATING DESORBED GAS IN PRODUCTION

(71) Applicant: SAUDI ARABIAN OIL COMPANY, Dhahran (SA)

(72) Inventors: Pan Luo, Dhahran (SA); Moemen A. Abdelrahman, Dhahran (SA); Rabah Mesdour, Dhahran (SA); Abdulbari N. Alhayaf, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 514 days.

(21) Appl. No.: 17/727,580

(22) Filed: Apr. 22, 2022

(65) Prior Publication Data
US 2023/0340876 A1    Oct. 26, 2023

(51) Int. Cl.
  *E21B 49/08*   (2006.01)
  *G01N 33/28*   (2006.01)
  *G01V 9/00*    (2006.01)

(52) U.S. Cl.
  CPC ........ *E21B 49/088* (2013.01); *E21B 49/0875* (2020.05); *G01N 33/2823* (2013.01);
  (Continued)

(58) Field of Classification Search
  CPC ............... E21B 49/088; E21B 49/0875; E21B 2200/20; G01N 33/2823; G01N 33/2841; G01V 9/007
  See application file for complete search history.

(56) References Cited

U.S. PATENT DOCUMENTS

| | | |
|---|---|---|
| 6,860,147 B2 | 3/2005 | Gunter et al. |
| 7,369,979 B1 | 5/2008 | Spivey |

(Continued)

FOREIGN PATENT DOCUMENTS

| | | |
|---|---|---|
| WO | 2019178432 A1 | 9/2019 |
| WO | 2020122746 A1 | 6/2020 |

OTHER PUBLICATIONS

N. S. Alharthy et al.; "Multiphase Compositional Modeling in Small-Scale Pores of Unconventional Shale Reservoirs", SPE-166306-MS; Society of Petroleum Engineers; Sep. 30, 2013; pp. 1-20 (20 pages).

(Continued)

*Primary Examiner* — Catherine T. Rastovski
*Assistant Examiner* — Yossef Korang-Beheshti
(74) *Attorney, Agent, or Firm* — Osha Bergman Watanabe & Burton LLP (57) ABSTRACT

Methods and systems for determining an estimated reservoir property using a determined desorption stage are disclosed. The method includes determining a fluid property and composition of a first fluid sample obtained from a reservoir, determining a measured relative volume of gas components and isotope ratios of gas components of the sample, and determining an equation of state. The method also includes obtaining a second and third sample at two later times, determining a composition, a measured relative volume of gas components, and isotope ratios of gas components of the later samples, and calibrating the equation of state utilizing the fluid composition and measured relative volume of gas components. The method further includes predicting a relative volume of gas components from the equation of state, determining a desorption stage, determining a critical pressure, an extent of desorption and a quantity of produced (Continued)

desorbed gas and determining the estimated reservoir property.

10 Claims, 8 Drawing Sheets

(52) U.S. Cl.
CPC ......... *G01N 33/2841* (2013.01); *G01V 9/007* (2013.01); *E21B 2200/20* (2020.05)

(56) References Cited

U.S. PATENT DOCUMENTS

| | | | |
|---|---|---|---|
| 9,790,770 B2 | 10/2017 | King et al. | |
| 10,140,393 B2 | 11/2018 | Hoda et al. | |
| 10,280,722 B2 | 5/2019 | Bello et al. | |
| 10,416,349 B2 | 9/2019 | Bang et al. | |
| 10,822,938 B2 | 11/2020 | Zhu et al. | |
| 2012/0053838 A1* | 3/2012 | Andrews | E21B 49/10 73/23.35 |
| 2015/0198039 A1* | 7/2015 | Marshall | E21B 21/067 73/152.42 |
| 2016/0259087 A1* | 9/2016 | Siddiqui | E21B 43/34 |
| 2017/0107814 A1* | 4/2017 | Dinariev | G01N 33/241 |
| 2021/0002991 A1 | 1/2021 | Morsy et al. | |
| 2021/0047924 A1* | 2/2021 | Kallehbasti | G01N 21/31 |

OTHER PUBLICATIONS

R. Altman et al.; "Understanding Mechanisms for Liquid Dropout from Horizontal Shale Gas Condensate Wells", SPE-170983-MS; Society of Petroleum Engineers; Oct. 27, 2014; pp. 1-17 (17 pages).
R. J. Ambrose et al.; "Multi-component Sorbed-phase Considerations for Shale Gas-in-place Calculations", SPE 141416; Society of Petroleum Engineers; Mar. 27, 2011; pp. 1-10 (10 pages).
C. Boyer et al.; "Producing Gas from Its Source", Oil Review; 2006; pp. 36-49 (14 pages).
M. Faiz et al.; "Compositional variations and carbon isotope reversal in coal and shale gas reservoirs of the Bowen and Beetaloo basins, Australia", Application of Analytical Techniques to Petroleum Systems; The Geological Society of London; vol. 484; Oct. 19, 2020 (20 pages).
L. Gao et al.; "The gas isotope interpretation tool: A novel method to better predict production decline", AAPG Bulletin; vol. 101; No. 8; Aug. 2017; pp. 1263-1275 (13 pages).
F. Hao et al.; "Mechanisms of shale gas storage: Implications for shale gas exploration in China", AAPG Bulletin; vol. 97; No. 8; Aug. 2013; pp. 1325-1346 (22 pages).
D. Strapoc et al.; "Carbon isotopic fractionation of CH4 and CO2 during canister desorption of coal", Organic Geochemistry; vol. 37; Issue 2; Dec. 7, 2005; pp. 152-164 (13 pages).
G W. van Graas et al.; "The effects of phase fractionation on the composition of oils, condensates and gases", Organic Geochemistry; vol. 31; Dec. 1, 2000; pp. 1419-1439 (21 pages).
Hanyi Wang; "What Factors Control Shale-Gas Production and Production-Decline Trend in Fractured Systems: A Comprehensive Analysis and Investigation", SPE 179967; SPE Journal; Apr. 2017; pp. 562-581 (20 pages).
X. Wang et al.; "Carbon isotopic fractionation by desorption of shale gases", Marine and Petroleum Geology; vol. 60; Dec. 4, 2014; pp. 79-86 (8 pages).
X. Xia and G. S. Ellis; "Coupled Kinetic and Fluid Dynamic Models to Understand H2S Occurence in Unconventional Petroleum Reservoirs", URTeC: #2460230; Unconventional Resources Technology Conference; Aug. 1, 2016; pp. 1-10 (10 pages).
K. Xia and Y. Tang; "Isotope fractionation of methane during natural gas flow with coupled diffusion and adsorption/desorption", Geochimica et Cosmochimica Acta; vol. 77; Oct. 17, 2011 (17 pages).
M. Zhang et al.; "Molecular and carbon isotopic variation in 3.5 years shale gas production from Longmaxi Formation in Sichuan Basin, China", Marine and Petroleum Geology; Jan. 30, 2017; pp. 27-37 (11 pages).
C.M. Freeman et al.; "Modeling and Performance Interpretation of Flowing Gas Composition Changes in Shale Gas Wells with Complex Fractures", IPTC 17075; International Petroleum Technology Conference; Mar. 2013; pp. 1-16 (16 pages).
R. Heller and M. Zoback; "Adsorption of methane and carbon dioxide on gas shale and pure mineral samples", Journal of Unconventional Oil and Gas Resources; vol. 8; Jul. 27, 2014; pp. 14-24 (11 pages).
I. Hutcheon et al.; "Inorganic origin of carbon dioxide during low temperature thermal recovery of bitumen: Chemical and isotopic evidence", Geochimica et Cosmochimica Acta; vol. 54; pp. 165-171 (7 Pages).
J. Jiang and R. M. Younis; "Compositional modeling of enhanced hydrocarbons recovery for fractured shale gas-condensate reservoirs with the effects of capillary pressure and multicomponent mechanisms", Journal of Natural Gas Science and Engineering; vol. 34; Aug. 4, 2016; pp. 1262-1275 (14 pages).
P. Lu et al.; "A mineral-water-gas interaction model of pCO2 as a function of temperature in sedimentary basins", Chemical Geology; vol. 558 (8 pages).
A. V. Milkov et al.; "Geochemistry of shale gases from around the world: Composition, origins isotopes reversals and rollovers, and implications for the exploration of shale plays", Organic Geochemistry; vol. 143; Feb. 26, 2020; pp. 1-18 (18 pages).
G. Norville et al.; "Insights from stable isotope geochemistry surveillance in the unconventional Horn River Basin play", URTeC: 2901086; Unconventional Resources Technology Conference; Sep. 28, 2018; pp. 1-18 (18 pages).
O. M. Olorode et al.; "Compositional Reservoir-Flow Simulation for Organic-Rich Gas Shale", SPE 182667; Society of Petroleum Engineers; Feb. 20, 2017; pp. 1963-1983 (21 pages).
JC Pashin; "Applied Coal Petrology—The Role of Petrology in Coal Utilization", Elsevier; Ch. 9; 2008; pp. 227-262 (36 pages).
N. Pedentchouk and C. Turich; "Carbon and hydrogen isotopic compositions of n-alkanes as a tool in petroleum exploration", From Source to Seep: Geochemical Applications in Hydrocarbon Systems; Dec. 14, 2017; pp. 105-125 (21 pages).
P. Pirzadeh et al.; "Hydraulic Fracturing Additives and the Delayed Onset of Hydrogen Sulfide in Shale Gas", Energy & Fuels; vol. 28; No. 8; pp. 4993-5001 (9 pages).
A. Prinzhofer et al.; "Geochemical Characterization of Natural Gas: A Physical Multivariable Approach and its Applications in Maturity and Migration Estimates", AAPG Bulletin; vol. 84; No. 8; Aug. 2000 (28 pages).
H. Qin et al.; "Carbon isotope reversal of desorbed gas in Longmaxi shale of Jiaoshiba area, Sichuan Basin", Petroleum Research; vol. 2; Issue 2; Jun. 2017; pp. 169-177 (9 pages).
V. Rajput and T. Ertekin; "Thermodynamically-Consistent Modeling of Adsorption in Liquid-Rich Shales", SPE-169589-MS; Society of Petroleum Engineers; Apr. 27, 2014; pp. 1-15 (15 pages).
V. Shabro et al.; "Numerical Simulation of Shale-Gas Production: from Pore-Scale Modeling of Slip-Flow, Knudsen Diffusion, and Langmuir Desorption to Reservoir Modeling of Compressible Fluid", SPE 144355; Society of Petroleum Engineers; Jun. 14, 2011; pp. 1-11 (11 pages).
W. Shi et al.; "Experimental study on gas content of adsorption and desorption in Fuling shale gas field", Journal of Petroleum Science and Engineering, vol. 180; Sep. 2019; pp. 1069-1076 (8 pages).
H. Singh and F. Javadpour; "Langmuir slip-Langmuir sorption permeability model of shale", Fuel; vol. 164; Jan. 2016; pp. 28-37 (10 pages).

\* cited by examiner

INTEGRATED TIME-LAPSE GAS GEOCHEMISTRY AND EQUATION OF STATE MODELING FOR EVALUATING DESORBED GAS IN PRODUCTION

BACKGROUND

Gas reservoirs located in shale rocks and coal beds are an important "unconventional" hydrocarbon resource. In the reservoirs, the gas is composed of free gas contained within pore space and adsorbed gas associated to the surface of grains, which are primarily comprised of kerogen and clay minerals. Gas adsorbed onto the surface of the grains is in equilibrium with free gas in the shale pores.

Estimating the quantity of desorbed gas during pressure depletion in production may be utilized to determine the reserve and ultimate recovery of gas in the unconventional reservoirs. The estimated parameters provide several variables for petroleum resource management and forming a reservoir development plan. In addition, estimating the critical pressure of gas desorption may be useful to predict production decline and compositional change for optimizing the hydraulic fracturing and production from unconventional reservoirs.

SUMMARY

This Summary is provided to introduce a selection of concepts that are further described in the Detailed Description. This summary is not intended to identify key or essential features of the claimed subject matter, nor is it intended to be used as an aid in limiting the scope of the claimed subject matter.

In general, in one aspect, embodiments relate to a method for determining an estimated reservoir property. The method includes determining a fluid property and a composition of a first fluid sample obtained at a first time from a sampling location associated with an unconventional hydrocarbon reservoir, determining a measured relative volume of gas components and isotope ratios of gas components of the first fluid sample, and determining an equation of state with the fluid property and the composition of the first fluid sample. The method also includes obtaining a second fluid and third fluid sample at a later second and third times from the unconventional hydrocarbon reservoir, determining a value of the fluid composition, a measured relative volume of gas components, and isotope ratios of gas components of the second and third fluid samples, and calibrating a parameter of the equation of state utilizing the fluid composition and the measured relative volume of gas components of the second and third fluid samples. The method further includes predicting a relative volume of gas components in a production flow based on the equation of state, determining for each fluid sample time, a desorption stage utilizing a temporal variation of gas isotope ratios and a sequence of isotope ratios between methane, ethane and propane, and determining a critical pressure and an extent of desorption utilizing a difference between the predicted relative volume of gas components from the measured relative volume of gas components. The method still further includes determining a quantity of produced desorbed gas under different pressures utilizing both the determined desorption stage and the difference between the predicted relative volume of gas components from the measured relative volume of gas components, and determining the estimated reservoir property utilizing a determined desorption stage, a critical desorption pressure, and quantity of produced desorbed gas.

In general, in one aspect, embodiments relate to a non-transitory computer readable medium storing instructions executable by a computer processor. The instructions include functionality for determining a fluid property and a composition of a first fluid sample received at a first time from a sampling location associated with an unconventional hydrocarbon reservoir, determining a measured relative volume of gas components and isotope ratios of gas components of the first fluid sample, and determining an equation of state with the fluid property and the composition of the first fluid sample. The instructions also include functionality for receiving a second fluid and third fluid sample at a later second and third times from the unconventional hydrocarbon reservoir, determining a value of the fluid composition, a measured relative volume of gas components, and isotope ratios of gas components of the second and third fluid samples, and calibrating a parameter of the equation of state utilizing the fluid composition and the measured relative volume of gas components of the second and third fluid samples. The instructions further include functionality for predicting a relative volume of gas components in a production flow based on the equation of state, determining for each fluid sample time, a desorption stage utilizing a temporal variation of gas isotope ratios and a sequence of isotope ratios between methane, ethane and propane, and determining a critical pressure and an extent of desorption utilizing a difference between the predicted relative volume of gas components from the measured relative volume of gas components. The instructions still further include functionality for includes determining a quantity of produced desorbed gas under different pressures utilizing both the determined desorption stage and the difference between the predicted relative volume of gas components from the measured relative volume of gas components, and determining the estimated reservoir property utilizing a determined desorption stage, a critical desorption pressure, and quantity of produced desorbed gas.

In general, in one aspect, embodiments relate to a system including a fluid sampling device configured to obtain a liquid sample and a gas sample at a plurality of sample times from an unconventional hydrocarbon reservoir, a chemical composition analyzer configured to detect a measured value of a parameter of the fluid sample obtained at the plurality of sample times, an isotope ratio analyzer configured to detect a measured value of a parameter of the fluid sample obtained at the plurality of sample times, a pressure-volume-temperature analyzer configured to detect a measured value of a parameter of the fluid sample obtained at the plurality of sample times, and a computer processor. The computer processor is configured to determine a fluid property and a composition of a first fluid sample, obtained at a first time from a sampling location associated with an unconventional hydrocarbon reservoir, determine a measured relative volume of gas components and isotope ratios of gas components of the first fluid sample, and determine an equation of state with the fluid property and the composition of the first fluid sample. The computer processor is also configured to receive a second fluid sample at a second time and a third fluid sample at a third time from the unconventional hydrocarbon reservoir, wherein the second time is after the first time and the third time is after the second time, determine a value of the fluid composition, a measured relative volume of gas components, and isotope ratios of gas components of the second fluid sample and the third fluid sample, and calibrate a parameter of the equation of state utilizing the fluid composition and the measured relative volume of gas components of the second fluid sample and the third fluid sample. The computer is further configured to predict a predicted relative volume of gas components in a production flow based, at least in part, on the equation of state, determine for each fluid sample time, a desorption stage utilizing a temporal variation of gas isotope ratios and a sequence of isotope ratios between methane, ethane and propane, and determine a critical pressure and an extent of desorption utilizing a difference between the predicted relative volume of gas components from the measured relative volume of gas components. The computer is still further configured to determine a quantity of produced desorbed gas under different pressures utilizing both the determined desorption stage and the difference between the predicted relative volume of gas components from the measured relative volume of gas components; and determine an estimated reservoir property utilizing a determined desorption stage, a critical desorption pressure, and quantity of produced desorbed gas.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

In the following Detailed Description, numerous specific details are set forth in order to provide a more thorough understanding of the disclosure. However, it will be apparent to one of ordinary skill in the art that the disclosure may be practiced without these specific details. In other instances, well-known features and typical knowledge and skill of the art have not been described in detail to avoid unnecessarily complicating the Detailed Description.

Throughout the application, ordinal numbers (for example, first, second, and third) may be used as an adjective for an element (that is, any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed, precede, or be performed simultaneously with, the second element in an ordering of elements.

Numerical models are available to describe the equilibrium between free and adsorbed gas and the transformation of desorbed gas to free gas, called "desorption", as temperature and pressure of the reservoir changes. However, without the measurement of key characteristics of desorption it is difficult to determine critical parameters, to calibrate the models, and to validate their predictions.

The disclosed embodiments describe methods and systems for determining the value of reservoir parameters controlling the amount and behavior of desorbed gas in an unconventional reservoir. The embodiments describe a method to determine desorption stage and identify the desorbed gas during production by using isotope fingerprint of the gas. The embodiments describe the calibration of an equation of state (EoS) for modeling, fluid phase behavior, and compositional change in the production from an unconventional reservoir based, at least in part, on pressure-volume-temperature (PVT) and chemical analysis of fluid samples taken at or near the beginning of production. Further, the prediction of the value of at least one parameter of the produced gas at a later time is disclosed. The methods for determining the value of the reservoir parameters based on the difference between predicted and the detected value of a parameter of a gas sample a later time is disclosed.

The hydrocarbon gas within the pores located in shale reservoirs may be termed "free gas" and the gas attached to the surface of shale grains may be termed "adsorbed gas". Together the free gas and the adsorbed gas make up the total hydrocarbon gas in place that may be available to be produced from the reservoir. Under static reservoir conditions, such as static pressure and temperature, free gas and adsorbed gas are in thermodynamic equilibrium.

Several numerical models are well known to one of ordinary skill in the art to describe the equilibrium between free and adsorbed gas and the transformation of desorbed gas to free gas, a process called "desorption", as the temperature and pressure of the reservoir changes during production. For example, the Freundlich adsorption isotherm describes an adsorption model for rough surfaces. The Temkin adsorption isotherm further accounts for indirect interactions between the adsorbed molecules. The Brunauer-Emmett-Teller (BET) equation includes multiple layer adsorption. A widely used model describing the equilibrium between free and adsorbed gas is the Langmuir adsorption isotherm.

Figure 1:
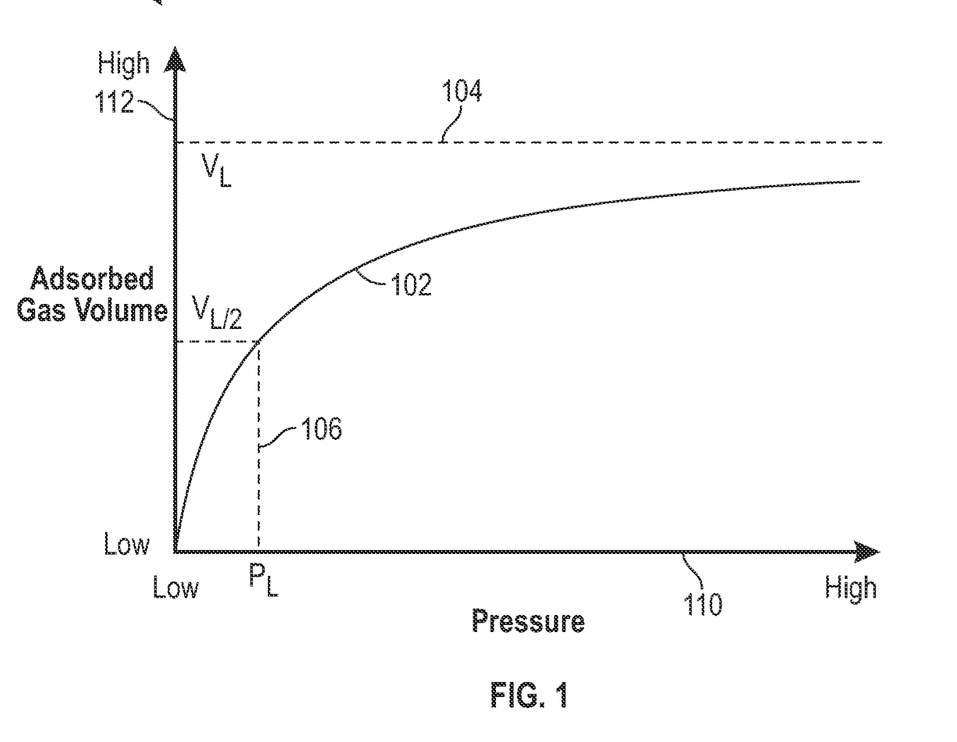
FIG. 1 shows a Langmuir isotherm in accordance with one or more embodiments.

FIG. 1 shows a Langmuir adsorption isotherm in accordance with one or more embodiments. The Langmuir adsorption isotherm (102) shown in plot (100) is a widely used model for describing the behavior of adsorbed hydrocarbon gas in a shale model. The Langmuir adsorption isotherm (102) predicts the amount of adsorbed gas, indicated on the vertical axis (112), as a function of the reservoir pressure, indicated on the horizontal axis (110). The adsorbed gas may be measured in units of cubic feet of gas at standard pressure and temperature conditions ("scf") per ton of reservoir rock. At infinitely high pressures, the Langmuir adsorption isotherm asymptotes to the Langmuir volume (104), $V_L$, the amount of gas that may be adsorbed at infinite pressure. The Langmuir pressure (106), $P_L$, may be defined as the pressure at which the volume of adsorbed gas is half the Langmuir volume (104). The Langmuir pressure (106) is also known as the "critical desorption pressure".

For a single gas, such as methane, the Langmuir isotherm may be written as shown in Equation (1):

$$V = \frac{V_L p}{P_L + p} \quad \text{Equation (1)}$$

where V is volume of adsorbed gas per unit reservoir rock and p is the reservoir pressure.

However, in accordance with one or more embodiments, the natural gas present in gas reservoirs may be a composite of methane ($CH_4$), ethane ($C_2H_6$), propane ($C_3H_8$), and greater hydrocarbon molecules. As well, non-hydrocarbon gases, such as, but not limited to, carbon dioxide ($CO_2$), hydrogen sulfide ($H_2S$), and nitrogen ($N_2$), may also be present in significant concentrations in some formations. In these circumstances, each gas does not adsorb independently; rather, they compete for the same adsorption sites on the mineral or grain surfaces. Consequently, the sum of the adsorbed volume of each component is less than when any of the gases acts independently. A multi-component gas adsorption isotherm is needed in order to predict the produced gas composition, gas-in-place, production rates, and estimated ultimate recovery (EUR).

A multi-component gas adsorption isotherm for an n-component gas may be expressed as Equation (2):

$$V_i = V_{L_i} \frac{p_i/P_{L_i}}{1 + \sum_{j=1}^{n} p_j/P_{L_j}} \quad \text{Equation (2)}$$

where $V_i$ is the volume of the i-th gas, $V_{L_i}$ is the Langmuir volume of the i-th gas, $p_i$ is the partial pressure of the i-th gas, and $P_{L_i}$ is the Langmuir pressure of the i-th gas. Defining the parameters in Equation (2), specifically the Langmuir volume and Langmuir pressure, for each component of the natural gas is useful to predict the produced gas composition, gas-in-place, production rates, and EUR.

Figure 2A:
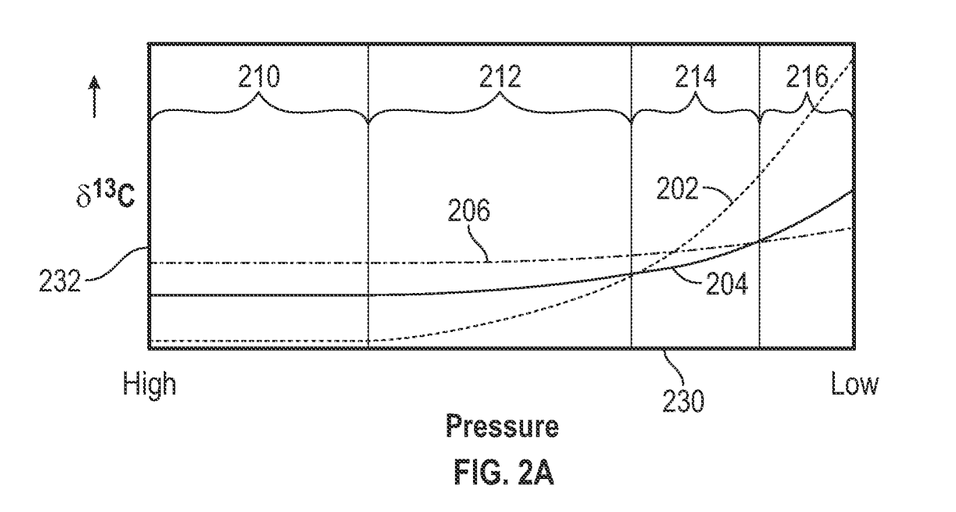
FIGS. 2A-2C show isotope ratio, molecular composition, and wetness variation of desorbed gas, respectively, in accordance with one or more embodiments.
Figure 2B:
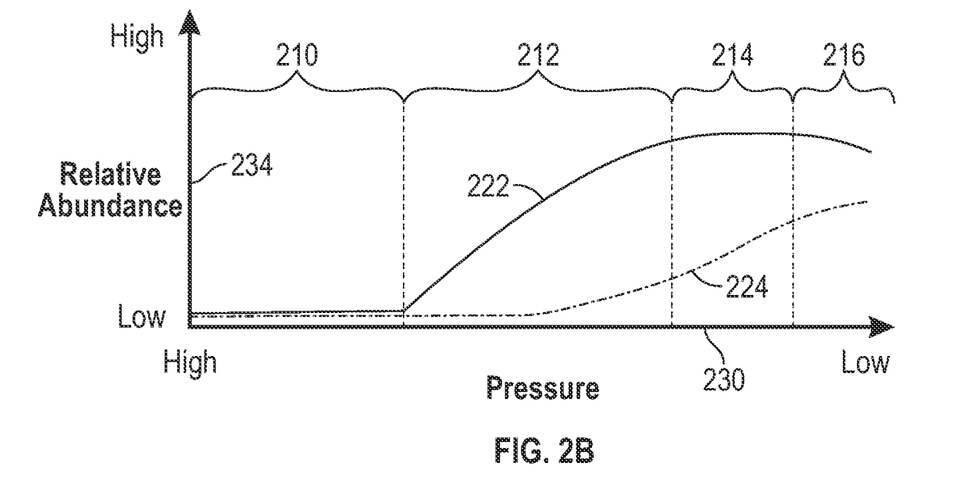
Figure 2C:
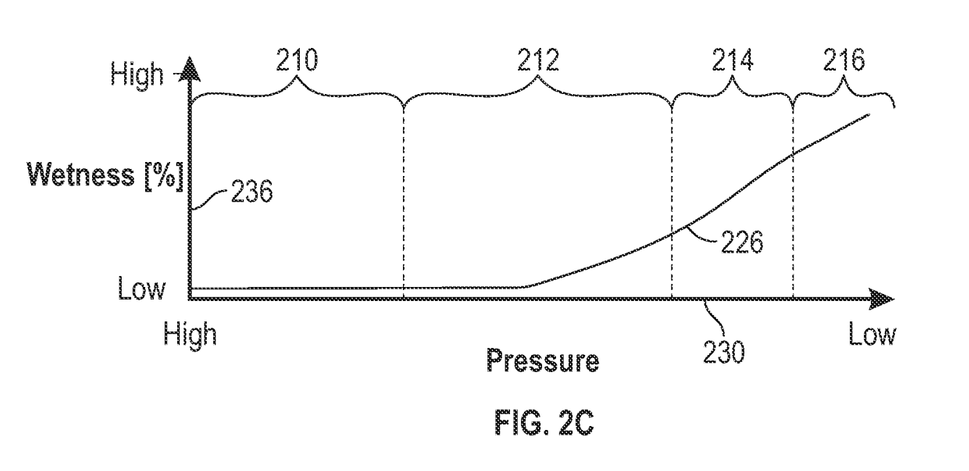

FIGS. 2A-2C show isotope ratio, molecular composition, and wetness variation of desorbed gas, respectively, in accordance with one or more embodiments. FIG. 2A shows the isotopic variation of desorbed gas with pressure. In FIG. 2A, the isotopic ratio is shown on vertical axis (232) and reservoir pressure is shown on the horizontal axis (230).

FIG. 2B shows the variation of molecular composition of desorbed gas with pressure. In FIG. 2B, relative abundance is shown on vertical axis (234) and reservoir pressure is shown on the horizontal axis (230).

FIG. 2C shows the variation of the "wetness" of desorbed gas with pressure. Percentage wetness is defined as the ratio of the abundance of all hydrocarbon molecules with more than one carbon atom ("polycarbon hydrocarbon gas") divided by the abundance of all hydrocarbon gases, that is, methane plus polycarbon hydrocarbon gas. In FIG. 2C, wetness is shown on vertical axis (236) and reservoir pressure is shown on the horizontal axis (230).

In FIGS. 2A-2C, the reservoir pressure decreases from left to right, thus the reservoir pressure is greater on the left-hand side and reduced on the right-hand side. Typically, the pressure of a reservoir decreases over time as the hydrocarbons within it are produced. Therefore, the horizontal axis (230) may also be regarded as a monotonic but nonlinear proxy for production time. In such a case, the earlier times being on the left-hand side and later times on the right-hand side of FIG. 2A. However, in some cases, steps to maintain or increase the reservoir pressure, for example, the injection of water into the reservoir, may be taken during production. In such cases, reservoir pressure may not decrease monotonically with time during production.

FIG. 2A shows the isotopic ratio values, $\delta^{13}$ C, of methane (202), ethane (204), and propane (206) in the desorbed gas as a function of pressure. In accordance with one or more embodiments, at an initial reservoir pressure the $\delta^{13}$ C value of methane, denoted as $\delta^{13}$ $C_1$, is less than the $\delta^{13}$ C value of ethane, denoted as $\delta^{13}$ $C_2$, which is in turn lower than the $\delta^{13}$ C value of propane, denoted as $\delta^{13}$ $C_3$. Therefore, at this condition $\delta^{13}$ $C_1 < \delta^{13}$ $C_2 < \delta^{13}$ $C_3$. This high-pressure or early-time portion of FIG. 2 may be termed the "pre-desorption" window (210).

As the reservoir pressure decreases, the value of $\delta^{13}$ $C_1$ begins to increase until $\delta^{13}$ $C_1 = \delta^{13}$ $C_2$. This portion of FIG. 2 may be called the "early desorption" window (212). Within the early desorption window, the relationship $\delta^{13}$ $C_1 \leq \delta^{13}$ $C_2 < \delta^{13}$ $C_3$ still holds.

As reservoir pressure decreases still further, the value of $\delta^{13}$ $C_1$ increases more rapidly than the rate of increase of $\delta^{13}$ $C_1$ at reducing pressures or extended production time. As well, the value of $\delta^{13}$ $C_2$ also begins to increase until $\delta^{13}$ $C_2 = \delta^{13}$ $C_3$. This portion of FIG. 2, where $\delta^{13}$ $C_1 > \delta^{13}$ $C_2$ and $\delta^{13}$ $C_2 \leq \delta^{13}$ $C_3$, may be termed the "significant desorption" window (214).

Finally, at a significantly reduced reservoir pressure, the relationship between the magnitudes $\delta^{13}$ $C_1$, $\delta^{13}$ $C_2$, and $\delta^{13}$ $C_3$ is fully reversed compared to the pre-desorption window (210) period, that is, $\delta^{13}$ $C_1 > \delta^{13}$ $C_2 > \delta^{13}$ $C_3$. This portion of FIG. 2 may be called the "deep desorption" window (216).

As shown in FIGS. 2B and 2C, during the pre-desorption window (210) the amounts of methane (222), polycarbon hydrocarbon gas (224), and wetness of the desorbed gas (226) remain relatively low. However, within the early desorption window (212), the amount of methane desorbed (222) increases rapidly while the desorption of polycarbon gases (224) and the wetness (226) of the desorbed gas increases little, if at all. Within the significant desorption window (214), the desorption of methane (222) ceases to increase while the desorption of polycarbon gases (224) increases steadily. In addition, an associated increase in the wetness (226) of the total desorbed gas occurs during this period. Finally, within the deep desorption window (216), the desorption of methane (222) decreases while the desorption of polycarbon gases (224) continues to increase. This condition results in an accelerated increase in the wetness (226) of the total desorbed gas.

FIGS. 2A-C together essentially present an ideal model of the chemical and isotopic composition of desorbed gases from an unconventional reservoir over time based upon depletion of formation pressure. Actual gas samples collected from the wellhead, the separator or the gas oil separation plant (GOSP) associated with an unconventional reservoir are a mixture of desorbed gas from the grain surface and free gas in the pores within the reservoir. Consequently, the isotopic and compositional signals of the various stages of desorption may be modified, hidden, or masked by this mixing. As a result, simple measurement of the chemical and isotopic composition of a sample drawn from the production flowline may be insufficient to unambiguously indicate the stage of desorption of the reservoir at the time of sampling.

In accordance with one or more embodiments, fluid samples (gas, oil, or both) produced from the reservoir may be collected at any position between downhole and the GOSP, such as at the wellhead or the separator. Samples produced from the reservoir may be taken at a plurality of times. A sample may be taken at a first time. The first time may be shortly after the completion of the well or the first production. The sample taken at this first time will be referred to as an "initial" gas sample. "Subsequent" samples may be taken at later times after the initial sample. Samples may be taken a regular or irregular time intervals. Samples may be taken according to a predetermined schedule or in response to changing production conditions, such as a change in flow rates. The fluid samples may be collected at times separated by days, weeks, months, or years.

In accordance with one or more embodiments, at least one fluid samples may be subjected to analysis. In particular, the initial sample may be subjected to PVT analysis. The analysis may include, without limitation, compositional analysis and constant volume depletion (CVD) analysis.

In accordance with one or more embodiments, compositional analysis may include the determination of the relative concentration of methane ($CH_4$) and the polycarbon hydrocarbon gases, such as ethane ($C_2H_6$), propane ($C_3H_8$), butanes ($C_4H_{10}$), pentanes ($C_5H_{12}$), hexanes ($C_6H_{14}$) and hydrocarbon molecules containing seven or more carbon atoms. Compositional analysis may further include, in accordance with one or more embodiments, the determination of the relative abundance of non-hydrocarbon gases, including, but not limited to, nitrogen ($N_2$), carbon dioxide ($CO_2$), and hydrogen sulfide ($H_2S$). In accordance with one or more embodiments, the relative concentration of groups of gas may be determined. For example, the relative concentration of a group of non-hydrocarbon gases, such as nitrogen ($N_2$), carbon dioxide ($CO_2$), and hydrogen sulfide ($H_2S$), may be determined. Further, the relative abundance of a group of light hydrocarbon gases, including methane ($CH_4$), ethane ($C_2H_6$), propane ($C_3H_8$), butanes ($C_4H_{10}$), pentanes ($C_5H_{12}$), and hexanes ($C_6H_{14}$), may be determined. Still further, the relative concentration of a group of all the hydrocarbon molecules that comprise seven or more carbon atoms may be determined.

In accordance with one or more embodiments, PVT analysis may determine the behavior of a fluid sample as the pressure, the temperature, and the volume of the sample is varied. PVT analysis may determine the critical pressure, critical temperature and saturation pressure of the sample.

CVD analysis of the sample may be designed to simulate hydrocarbon behavior in the pores of the reservoir as pressure decreases to less than the saturation pressure of the gas sample. In particular, the CVD analysis may be designed to characterize the liquid condensation behavior as the reservoir pressure decreases.

In accordance with one or more embodiments, an EoS may be used to determine the characteristics of a hydrocarbon fluid at a variety of pressures and temperatures. An EoS may determine properties of the produced hydrocarbon fluid and the phase separation as measured at a surface location, such as the wellhead or a GOSP. An EoS may determine the properties and phase of hydrocarbon fluid in the reservoir at a given set of conditions, which may be correlated with a time.

In accordance with one or more embodiments, the EoS may be the Peng-Robinson EoS. In accordance with other embodiments, the EoS may be selected from, but not limited to, the Redlich-Kwong EoS, the Soave-Redlich-Kwong EoS, the Zudkevitch-Joffe EoS, and derivations thereof.

For example, the Peng-Robinson EoS may be written as shown in Equation (3):

$$P = \frac{RT}{v-b} - \frac{a}{v(v+b) - b(v-b)} \qquad \text{Equation (3)}$$

where P is pressure, T is temperature, R is the universal gas constant, and v is the molar volume. The other factors of the Peng-Robinson EoS are defined in Equations (4-8):

$$a = a_c \alpha \qquad \text{Equation (4)}$$

$$\alpha = \left[1 + \kappa\left(1 - \sqrt{\frac{T}{T_c}}\right)\right]^2 \qquad \text{Equation (5)}$$

$$\kappa = 0.37464 + 1.5422\omega - 0.26992\omega^2 \qquad \text{Equation (6)}$$

$$a_c = \Omega_a \frac{R^2 T_c^2}{P_c} \qquad \text{Equation (7)}$$

$$b = \Omega_a \frac{RT_c}{P_c} \qquad \text{Equation (8)}$$

where $T_c$ is a critical temperature, $P_c$ is a critical pressure, $\Omega_a$ is an attraction coefficient, and $\omega$ is an acentric factor. These parameters may be determined experimentally from a gas sample, from literature or standard references, or a combination thereof.

In accordance with one or more embodiments, the EoS may be calibrated or "tuned" by varying the parameters required to fully specify the EoS. Tuning permits the model to accurately predict characteristics of a gas sample as determined from PVT testing such a gas sample, including, but not limited to, using CVD and compositional analyses of a fluid sample. The EoS tuning may be performed initially using an initial sample. In accordance with other embodiments, the initial EoS tuning may be corrected, revised, or updated based on the PVT, CVD, and compositional analyses of subsequent gas sample collected at later times during the producing life of the reservoir. Once tuned, the EoS may be used to predict, model, or simulate the characteristics of produced fluid phase and composition at the wellhead, the separator, or the GOSP, at future times and at different conditions, such as temperatures and pressures.

Figure 3A:
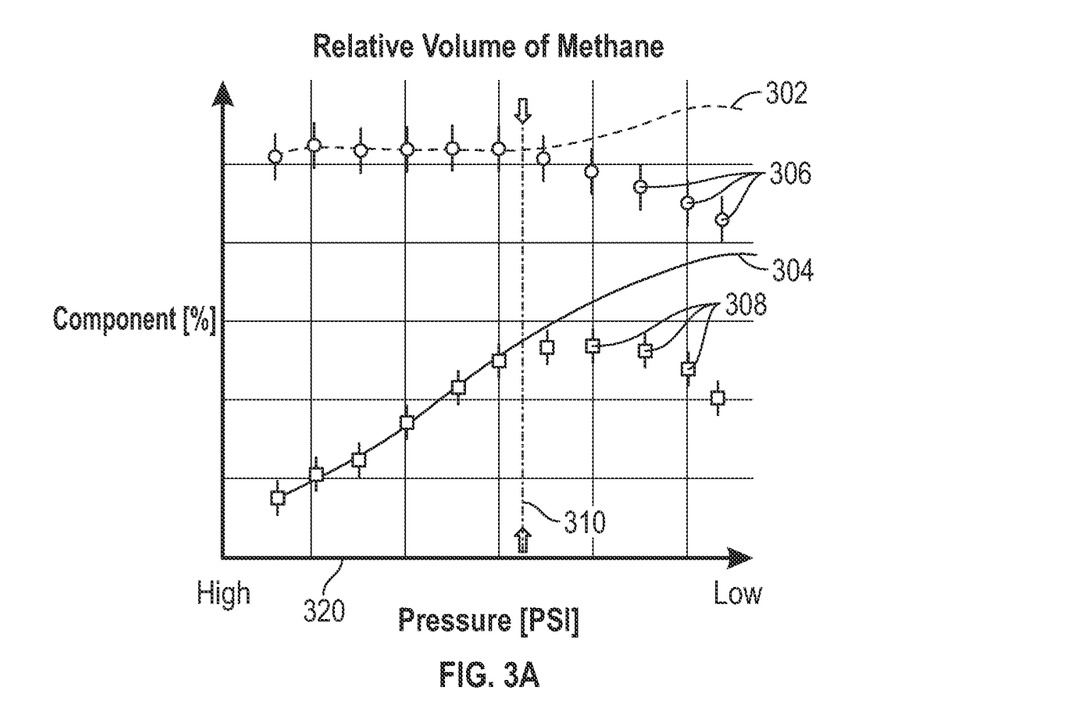
FIG. 3A shows both predicted trendlines for and actual measured relative volumes of methane in the fluid samples collected at the wellhead or separator at wellsite or the gas oil separation plant (GOSP) in the field during a sequence of time in accordance with one or more embodiments.

FIG. 3A shows both predicted trendlines for and actual measured relative volumes of methane (mol % or vol %) in samples collected at both the wellhead and the separator or GOSP during a sequence of time in accordance with one or more embodiments. The relative volume of methane in the samples collected at the separator or GOSP (302) and the wellstream or wellhead (304) can be measured and may change during the production at future times and different temperature and pressure conditions. In accordance with one or more embodiments, predicted trendlines for the relative volume of methane may be simulated by the EoS for the separator or GOSP gas samples (306) and in the wellstream or wellhead fluid samples (308) as shown in FIG. 3A. In accordance with one or more embodiments, these predicted trendlines (306, 308) and others may be made using the assumption that no desorbed gases are present in the actual samples taken.

At pressures greater (towards the left along the horizontal axis 320) than a critical pressure (310), the predicted trendlines of relative volume fraction of methane in the wellstream or wellhead fluid (308) correlates well with the measured relative volume fraction of methane in the wellstream or wellhead sample (304). Similarly, at pressures greater (towards the left along the horizontal axis 320) than a critical pressure (310), the predicted trendlines of relative volume of methane for the separator/GOSP gas flow (302) agrees well with the measured relative volume of methane in the gas sample taken from the separator/GOSP (306). However, at pressures less than the critical pressure (310), the predicted trendlines of relative volumes of methane at the separator/GOSP (302) and in the wellstream or wellhead (304) do not agree with the measured relative volumes of methane at both the separator/GOSP (306) and the wellstream or wellhead (308). The critical pressure may therefore be interpreted to be the pressure value at which desorption of methane from the formation material commences as the formation pressure declines through the critical pressure value. Thus, this critical pressure (310) may mark the boundary between the pre-desorption window (210) and the early desorption window (212), as previously depicted in FIG. 2.

Figure 3B:
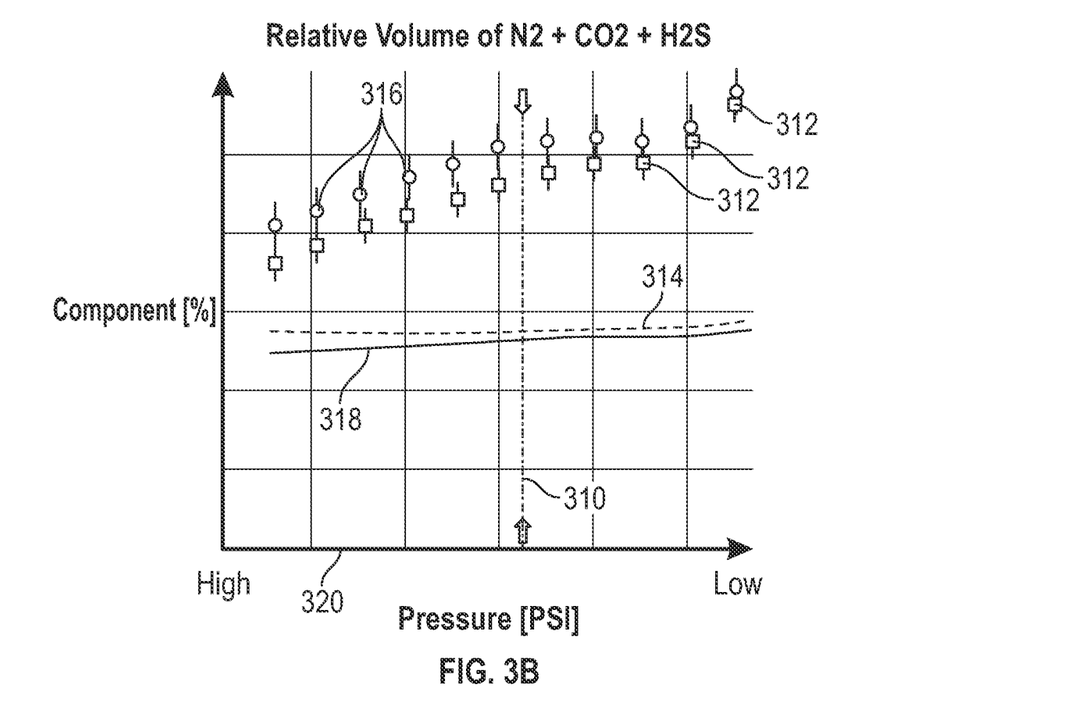
FIG. 3B shows both predicted trendlines for and actual measured relative volumes of non-hydrocarbon gas in the fluid samples at the wellhead, separator, or gas oil separation plant during a sequence of time in accordance with one or more embodiments.

FIG. 3B shows both predicted trendlines for and actual measured relative volume of non-hydrocarbon gas samples collected at both the wellstream or wellhead and the separator/GOSP during a sequence of time in accordance with one or more embodiments. FIG. 3B is similar to FIG. 3A in that it shows predicted trendlines for the combined relative volume of non-hydrocarbon gas consisting of nitrogen (N2), carbon dioxide (CO2), and hydrogen sulfide (H2S) at the wellstream or wellhead (318) and in the separator/GOSP (314). FIG. 3B also shows the relative volume of non-hydrocarbon gas measured in a plurality of gas samples collected at a sequence of times from the wellstream or wellhead (312) and collected at the separator/GOSP (316). As shown in FIG. 3B, the predicted relative volumes of non-hydrocarbon gas from the wellstream or wellhead (318) and the separator/GOSP (314) are constant during the production although the flow rate, temperature and pressure may change. In contrast, the measured relative volumes of non-hydrocarbon gas collected at the wellstream or wellhead (312) and the separator/GOSP (316) shows significant increase as the pressure decreasing during the production. Although not wanting to be bound by theory, the additional CO2 and H2S are probably generated by hydrolysis or sulfate reduction reaction induced by hydraulic fracturing in the shale reservoir. The non-hydrocarbon gases are not subject to desorption over this pressure range; however, methane is.

Figure 4:
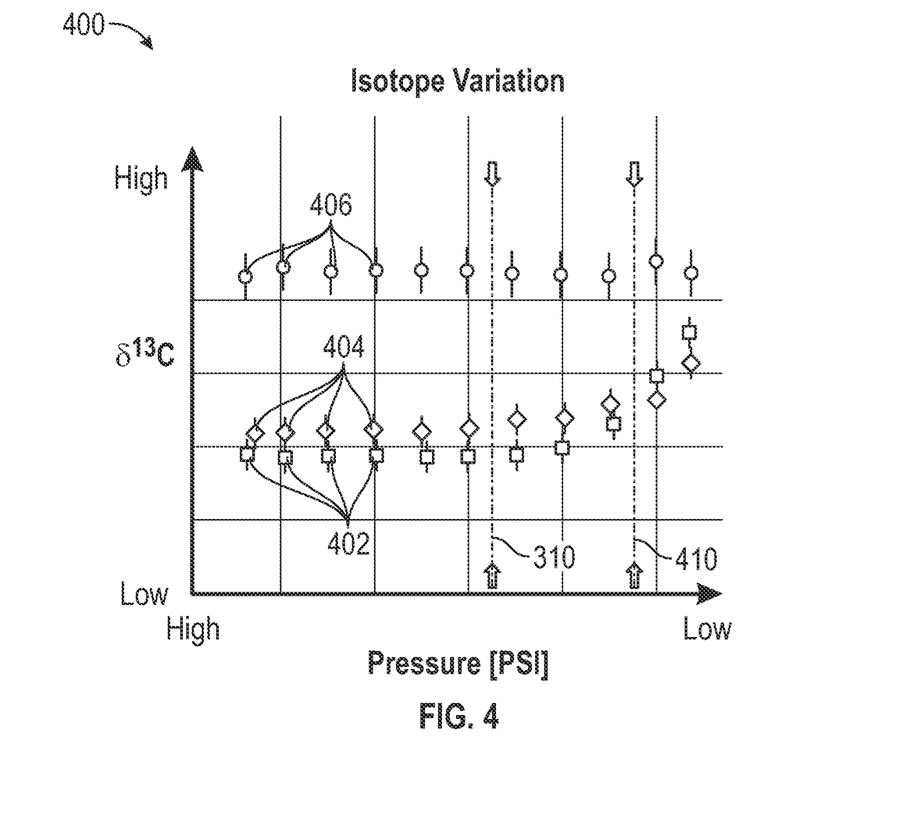
FIG. 4 shows isotope data in accordance with one or more embodiments.

FIG. 4 shows isotope data in accordance with one or more embodiments. FIG. 4 is a chart (400) with examples of the measured isotopic variation of samples of methane (402), ethane (404), and propane (406) gases as a function of reservoir pressure in the production from a shale reservoir. During early production, typically characterized by high reservoir pressure, the $\delta^{13}$ C values for methane (402), ethane (404), and propane (406) are constant, respectively, and present a normal relationship of isotopes $\delta^{13}$ $C_1 < \delta^{13}$ $C_2 < \delta^{13}$ $C_3$, indicating there is no contribution of desorbed gas into production as shown a "pre-desorption" window (210) in FIG. 2A. Typically, during production the reservoir pressure decreases and reaches the critical pressure (310) to start desorption. As reservoir pressure decreases the $\delta^{13}$ C values for each gas component may become larger, i.e., the negative values may become smaller negative values. In particular, a large increase in the $\delta^{13}$ C value for methane (402) may be observed, however the isotope relationship, $\delta^{13}$ $C_1 < \delta^{13}$ $C_2 < \delta^{13}$ $C_3$, remains unchanged. These isotopic characteristics define an "initial desorption" window (212) as shown in FIG. 2A in the gas production from a shale/coalbed reservoir, reflecting an initiation and increasing contribution of desorbed methane into the production. As depletion of reservoir continues and reservoir pressure falls further, the $\delta^{13}$ C values for each gas component increase further becoming more still less negative. The rapid increase of $\delta^{13}$ C values of methane (402) partially reverses the normal isotope relationship and lead to a relationship of $\delta^{13}$ $C_1 > \delta^{13}$ $C_2 < \delta^{13}$ $C_3$. This change of isotope relationship defines a transition pressure (410) from the initial desorption window (212) to a "significant desorption" window (214). In some situation where the reservoir pressure falls to low levels isotope relationship may be fully reversed ($\delta^{13}$ $C_1 > \delta^{13}$ $C_2 > \delta^{13}$ $C_3$), defining a "deep desorption" window (210) as shown in FIG. 2A. However, the fully reserved isotope relationship is rarely observed in the real production.

Figure 5:
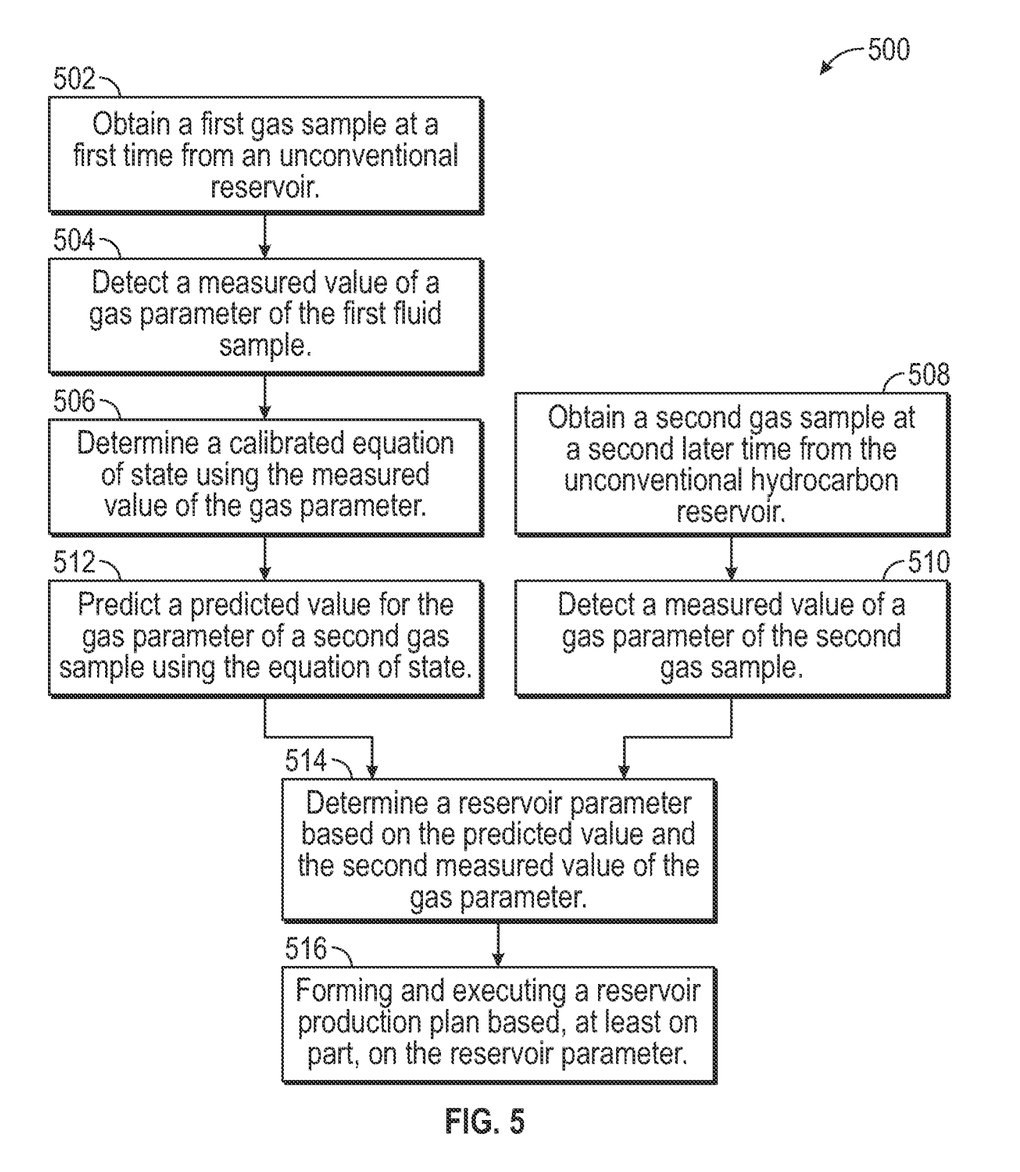
FIG. 5 shows a flowchart in accordance with one or more embodiments.

FIG. 5 shows a flowchart in accordance with one or more embodiment. The flowchart 500 begins in Step 502 where a first fluid sample is obtained as early as possible after clean-up, such as during well flowback or production from the unconventional reservoir. The sample may be collected in any location between downhole proximate to the unconventional reservoir to the GOSP, inclusive. In accordance with one or more embodiments, the sample may be collected at a wellhead. In accordance with other embodiments, the sample may be collected at a separator, at the wellsite, or a GOSP in the field. In accordance with an embodiment, the sample may be collected from a downhole location.

In accordance with one or more embodiments, in Step 504 measured values of fluid properties, chemical composition, and gas isotope ratios of the first fluid sample may be detected. The detection may use PVT analysis, including compositional analysis, CVD experimentation, and any common laboratory experiments used in determining fluid properties. The chemical composition of the fluid sample whose value is detected may be one or more parameter chosen from the relative volume of a plurality hydrocarbon gas components, the relative volume of a plurality of non-hydrocarbon gas components, and the isotopic ratio of carbon dioxide (CO2) and each hydrocarbon gas component.

In Step 506, in accordance with one or more embodiments, a calibrated EoS may be determined using the detected value of fluid properties and chemical composition determined in Step 504. In accordance with some embodiments, the EoS may be the Peng-Robinson EoS. In accordance with other embodiments, the EoS may be, without limitation, the Redlich-Kwong EoS, the Soave-Redlich-Kwong EoS, the Zudkevitch-Joffe EoS, and derivations thereof.

In Step 508, a second fluid sample may be obtained at a second time in the production flow from the unconventional hydrocarbon reservoir. The second time may be later than the first time and may be after a period of gas production from the reservoir. The reservoir pressure at the second time may be a different pressure than the reservoir pressure at the first time. The reservoir pressure at the second time may be a reduced pressure compared to the reservoir pressure at the first time.

In accordance with one or more embodiments, in Step 510 measured values of chemical composition and gas isotope ratios of the second fluid sample may be detected. The fluid parameter whose value is detected may be one or more parameter chosen from the relative volume of a plurality hydrocarbon components, the relative volume of a plurality of non-hydrocarbon gas components, and the isotopic ratio of carbon dioxide and each hydrocarbon gas component. The fluid parameter whose value is detected for the second sample may be the same fluid parameter whose value is detected for the first sample.

In Step 512, the chemical composition of the second fluid sample acquired at the second time may be predicted using the calibrated EoS calibrated in Step 506. The predicted relative volume of each component for the second fluid sample may be the same value as detected in Step 510.

In Step 514, in accordance with one or more embodiments, the desorption window may be determined based on measured gas isotope ratios using the method demonstrated in FIG. 2A, FIG. 3A, and their description.

In Step 516, the predicted compositional values predicted for sequential times from Step 512 and the measured compositional values measured at sequential times from Step 510 are. The deviation of measured values from the predicted values may indicate a critical pressure for the initiation of the gas desorption in the production from unconventional reservoir has been reached. Further deviation of measured values from the predicted values may indicate that a transition pressure from significant desorption to deep desorption has been reached, as illustrated in FIGS. 2A, 2B, and 2C. In addition, the degree of desorption that has occurred in the reservoir between the collection of the first fluid sample and the subsequent fluid sample may be estimated in a qualitative or quantitative manner. The contribution of desorbed gas into the production may be estimated in a qualitative or quantitative manner. Further the calibration of the EoS may be confirmed, corrected, updated, or revised using the fluid parameter detected for the second fluid sample prior to predicting the value of a fluid parameter of a fluid sample collected at a third or subsequent time.

In Step 518, hydrocarbon reserve assessment may be improved and a development plan for an unconventional reservoir may be formed and executed based, at least in part, on the reservoir parameters determined in Step 516. In the prior art, Langmuir equation is commonly used to calculate adsorbed gas on kerogen. The accuracy is depending on the representative of a rock sample for the reservoir and the descriptive of the Langmuir equation for the adsorption-desorption process. Therefore, it is very difficult to quantify adsorbed gas in place for the subsurface formation, and the adsorbed gas in place does not mean the desorbed gas in the production. Embodiments disclosed provide a manner to estimate the quantity of desorbed gas at different pressures in real production. The estimation of desorbed gas may be utilized to revise the calculation of gas-in-place (GIP) and ultimate recovery (EUR) and calibrate the Langmuir equation and the model in reservoir simulation for adsorption-desorption process. In addition, the adsorbed gas initially distributed in the organic matter; however, it will not be desorbed into the nanopore space until the pore pressure declines to the desorption pressure. Embodiments disclosed provide a manner to determine the critical pressures for the initiation of desorption and the extent of desorption, which are the useful parameters for determining the strategy of well production and predicting compositional change and production decline for unconventional reservoirs.

Figure 6:
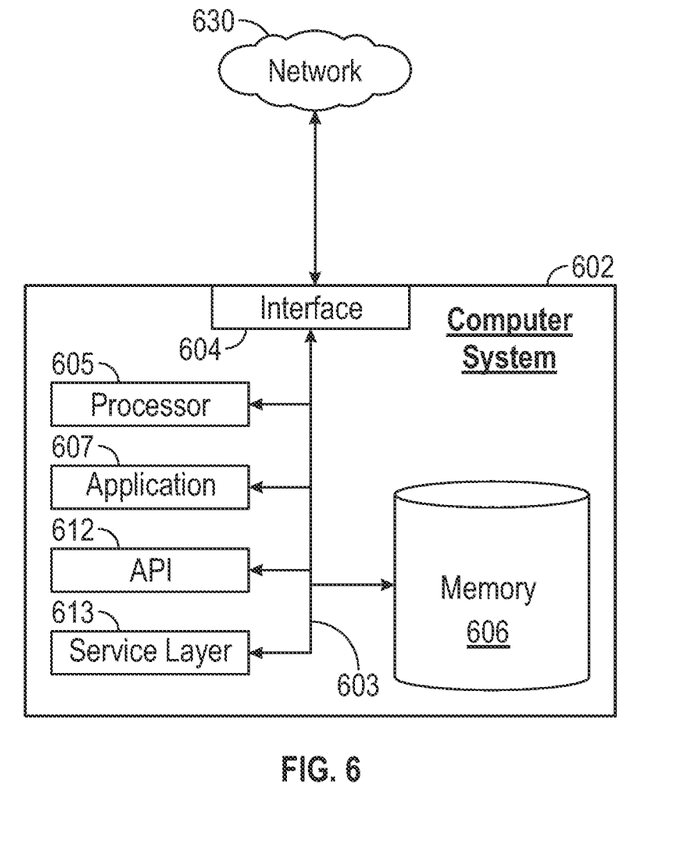
FIG. 6 shows a computer system in accordance with one or more embodiments.

FIG. 6 shows a computer system in accordance with one or more embodiments. FIG. 6 further depicts a block diagram of a computer system (602) used to provide computational functionalities associated with described algorithms, methods, functions, processes, flows, and procedures as described in this disclosure. The illustrated computer (602) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer system (602) may include a computer system that includes an input device, such as a keypad, keyboard, touch screen, or other device that can accept user information, and an output device that conveys information associated with the operation of the computer system (602), including digital data, visual, or audio information (or a combination of information), or a graphical user interface (GUI).

The computer system (602) can serve in a role as a client, network component, a server, a database or other persistency, or any other component (or a combination of roles) of a computer system (602) for performing the subject matter described in the instant disclosure. The illustrated computer system (602) is communicably coupled with a network (630). In some implementations, one or more components of the computer system (602) may be configured to operate within environments, including cloud-computing-based, local, global, or other environment (or a combination of environments).

At a high level, the computer system (602) is an electronic computing device operable to receive, transmit, process, store, or manage data and information associated with the described subject matter. According to some implementations, the computer system (602) may also include or be communicably coupled with an application server, e-mail server, web server, caching server, streaming data server, business intelligence (BI) server, or other server (or a combination of servers).

The computer system (602) can receive requests over network (630) from a client application (for example, executing on another computer system (602) and responding to the received requests by processing the said requests in an appropriate software application. In addition, requests may also be sent to the computer system (602) from internal users (for example, from a command console or by other appropriate access method), external or third-parties, other automated applications, as well as any other appropriate entities, individuals, systems, or computers.

Each of the components of the computer system (602) can communicate using a system bus (603). In some implementations, any or all of the components of the computer system (602), both hardware or software (or a combination of hardware and software), may interface with each other or the interface (604) (or a combination of both) over the system bus (603) using an application programming interface (API) (612) or a service layer (613) (or a combination of the API (612) and service layer (613). The API (612) may include specifications for routines, data structures, and object classes. The API (612) may be either computer-language independent or dependent and refer to a complete interface, a single function, or even a set of APIs. The service layer (613) provides software services to the computer system (602) or other components (whether or not illustrated) that are communicably coupled to the computer system (602). The functionality of the computer system (602) may be accessible for all service consumers using this service layer. Software services, such as those provided by the service layer (613), provide reusable, defined business functionalities through a defined interface. For example, the interface may be software written in JAVA, C++, or other suitable language providing data in extensible markup language (XML) format or another suitable format. While illustrated as an integrated component of the computer system (602), alternative implementations may illustrate the API (612) or the service layer (613) as stand-alone components in relation to other components of the computer system (602) or other components (whether or not illustrated) that are communicably coupled to the computer system (602). Moreover, any or all parts of the API (612) or the service layer (613) may be implemented as child or sub-modules of another software module, enterprise application, or hardware module without departing from the scope of this disclosure.

The computer system (602) includes an interface (604). Although illustrated as a single interface (604) in FIG. 6, two or more interfaces (604) may be used according to particular needs, desires, or particular implementations of the computer system (602). The interface (604) is used by the computer system (602) for communicating with other systems in a distributed environment that are connected to the network (630). Generally, the interface (604) includes logic encoded in software or hardware (or a combination of software and hardware) and operable to communicate with the network (630). More specifically, the interface (604) may include software supporting one or more communication protocols associated with communications such that the network (630) or interface's hardware is operable to communicate physical signals within and outside of the illustrated computer system (602).

The computer system (602) includes at least one computer processor (605). Although illustrated as a single computer processor (605) in FIG. 6, two or more processors may be used according to particular needs, desires, or particular implementations of the computer system (602). Generally, the computer processor (605) executes instructions and manipulates data to perform the operations of the computer system (602) and any algorithms, methods, functions, processes, flows, and procedures as described in the instant disclosure.

The computer system (602) also includes a memory (606) that holds data for the computer system (602) or other components (or a combination of both) that can be connected to the network (630). For example, memory (606) can be a database storing data consistent with this disclosure. Although illustrated as a single memory (606) in FIG. 6, two or more memories may be used according to particular needs, desires, or particular implementations of the computer system (602) and the described functionality. While memory (606) is illustrated as an integral component of the computer system (602), in alternative implementations, memory (606) can be external to the computer system (602).

The application (607) is an algorithmic software engine providing functionality according to particular needs, desires, or particular implementations of the computer system (602), particularly with respect to functionality described in this disclosure. For example, application (607) can serve as one or more components, modules, or applications. Further, although illustrated as a single application (607), the application (607) may be implemented as multiple applications (607) on the computer system (602). In addition, although illustrated as integral to the computer system (602), in alternative implementations, the application (607) can be external to the computer system (602).

There may be any number of computers (602) associated with, or external to, a computer system (602), wherein each computer (602) communicates over network (630). Further, the term "client," "user," and other appropriate terminology may be used interchangeably as appropriate without departing from the scope of this disclosure. Moreover, this disclosure contemplates that many users may use one computer system (602), or that one user may use multiple computer systems (602).

In some embodiments, reservoir simulator may be performed using the estimated reservoir properties for the unconventional hydrocarbon reservoir. For example, the reservoir simulator may include hardware and/or software with functionality for generating one or more reservoir models regarding the hydrocarbon-bearing formation and/or performing one or more reservoir simulations. For example, the reservoir simulator may store well logs and data regarding core samples for performing simulations. A reservoir simulator may further analyze the well log data, the core sample data, seismic data, and/or other types of data to generate and/or update the one or more reservoir models. In some embodiments, the reservoir simulator may include a computer that is similar to the computer (602) described above with regard to FIG. 6 and the accompanying description.

Figure 7A:
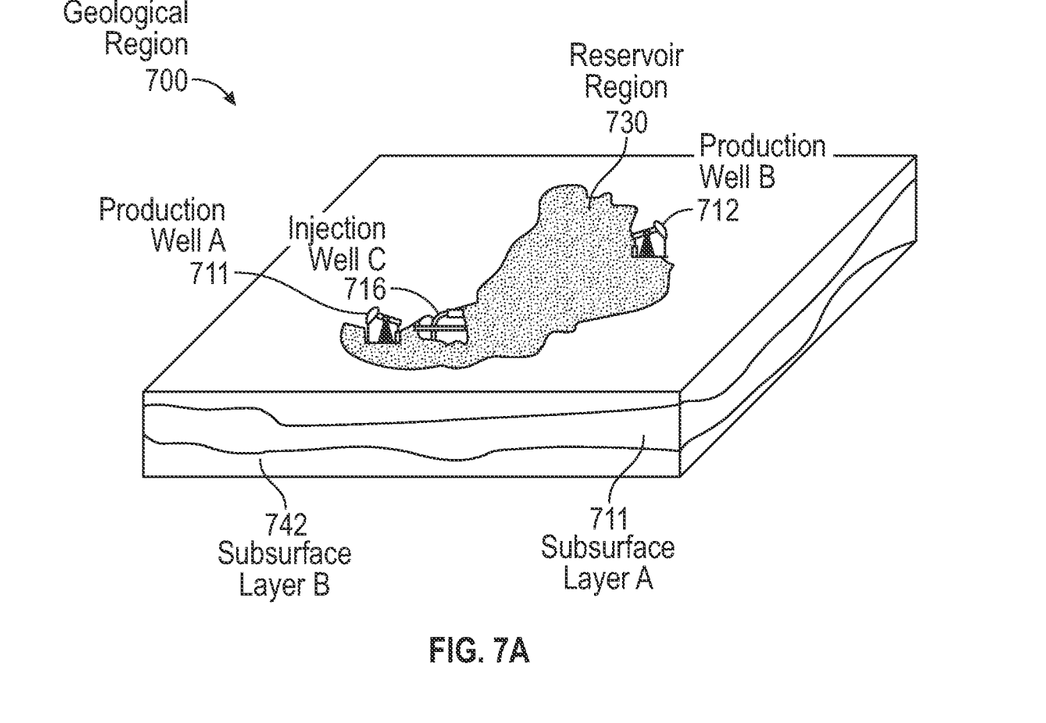
FIGS. 7A and 7B show reservoir simulation systems in accordance with one or more embodiments.

Turning to FIG. 7A, FIG. 7A shows a schematic diagram in accordance with one or more embodiments. As illustrated in FIG. 7A, FIG. 7A shows a geological region (700) that may include one or more reservoir regions (e.g., reservoir region (730)) with various production wells (e.g., production well A (711), production well (712)). Likewise, a reservoir region may also include one or more injection wells (e.g., injection well C (716)) that include functionality for enhancing production by one or more neighboring production wells. As shown in FIG. 7A, wells may be disposed in the reservoir region (730) above various subsurface layers (e.g., subsurface layer A (741), subsurface layer B (742)), which may include hydrocarbon deposits and unconventional reservoirs. In particular, production data and/or injection data may exist for a particular well, where production data may include data that describes production or production operations at a well, such as fluid properties and compositions of samples taken at the wellhead.

Figure 7B:
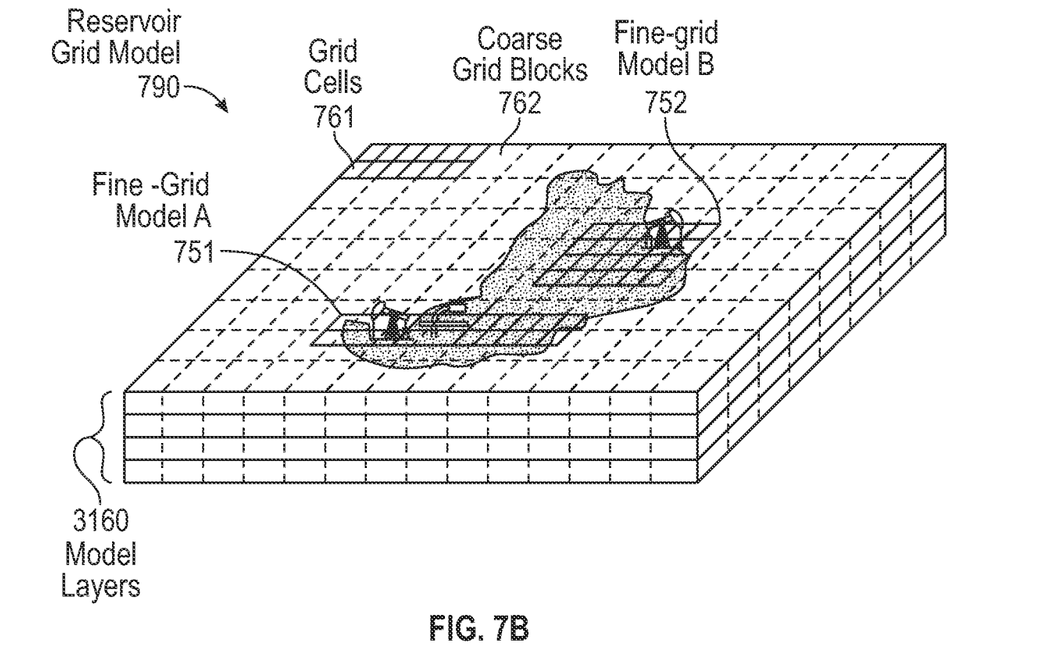

Turning to FIG. 7B, FIG. 7B shows a schematic diagram in accordance with one or more embodiments. As illustrated in FIG. 7B, FIG. 7B shows a reservoir grid model (790) that corresponds to the geological region (700) from FIG. 7A. More specifically, the reservoir grid model (790) includes grid cells (761) that may refer to an original cell of a reservoir grid model as well as coarse grid blocks (762) that may refer to an amalgamation of original cells of the reservoir grid model. For example, a grid cell may be the case of a 1×1 block, where coarse grid blocks may be of sizes 2×2, 4×4, 8×8, etc. Both the grid cells (761) and the coarse grid blocks (762) may correspond to columns for multiple model layers (760) within the reservoir grid model (790).

Prior to performing a reservoir simulation, local grid refinement and coarsening may be used to increase or decrease grid resolution in a certain area of reservoir grid model. For example, various reservoir properties, e.g., permeability, porosity or saturations, may correspond to a discrete value that is associated with a particular grid cell or coarse grid block. However, by using discrete values to represent a portion of a geological region, a discretization error may occur in a reservoir simulation. Thus, finer grids may reduce discretization errors as the numerical approximation of a finer grid is closer to the exact solution, however through a higher computational cost. As shown in FIG. 7B, for example, the reservoir grid model (790) may include various fine-grid models (i.e., fine-grid model A (751), fine-grid model B (752)), that are surrounded by coarse block regions. Likewise, the original reservoir grid model without any coarsening may also be a fine-grid model.

In some embodiments, proxy models or reduced-order models may be generated for performing a reservoir simulation. For example, one way to reduce model dimensionality is to reduce the number of grid blocks and/or grid cells. By averaging reservoir properties into larger blocks while preserving the flow properties of a reservoir model, computational time of a reservoir simulation may be reduced. In general, coarsening may be applied to cells that do not contribute to a total flow within a reservoir region because a slight change on such reservoir properties may not affect the output of a simulation. Accordingly, different levels of coarsening may be used on different regions of the same reservoir model. As such, a coarsening ratio may correspond to a measure of coarsening efficiency, which may be defined as a total number of cells in a coarse reservoir model divided by the original number of cells in the original reservoir model.

Flow properties, such as flux, may be defined as a reservoir fluid (e.g., oil or natural-gas) that flows between any two grid blocks. Likewise, grid cells or blocks may be upscaled in a method that reduces the computational demand on running simulations using fewer grid cells. However, a grid model may lose accuracy in a reservoir simulation if the underlying properties differ too much from the original fine-grid model.

In some embodiments, a reservoir simulator comprises functionality for simulating the flow of fluids, including hydrocarbon fluids such as oil and gas, through a hydrocarbon reservoir composed of porous, permeable reservoir rocks in response to natural and anthropogenic pressure gradients. The reservoir simulator may be used to predict changes in fluid flow, including fluid flow into well penetrating the reservoir as a result of planned well drilling, and fluid injection and extraction. For example, the reservoir simulator may be used to predict changes in hydrocarbon production rate that would result from the injection of water into the reservoir from wells around the reservoirs periphery.

The reservoir simulator may use a reservoir model that contains a digital description of the physical properties of the rocks as a function of position within the reservoir and the fluids within the pores of the porous, permeable reservoir rocks at a given time. In some embodiments, the digital description may be in the form of a dense 3D grid with the physical properties of the rocks and fluids defined at each node. In some embodiments, the 3D grid may be a cartesian grid, while in other embodiments the grid may be an irregular grid.

The physical properties of the rocks and fluids within the reservoir may be obtained from a variety of geological and geophysical sources. For example, remote sensing geophysical surveys, such as seismic surveys, gravity surveys, and active and passive source resistivity surveys, may be employed. In addition, data collected such as well logs, core data, production data as previously discussed, acquired in wells penetrating the reservoir may be used to determine physical and petrophysical properties along the segment of the well trajectory traversing the reservoir. For example, porosity, permeability, density, seismic velocity, and resistivity may be measured along these segments of wellbore. In accordance with some embodiments, remote sensing geophysical surveys and physical and petrophysical properties determined from well logs may be combined to estimate physical and petrophysical properties for the entire reservoir simulation model grid.

Reservoir simulators solve a set of mathematical governing equations that represent the physical laws that govern fluid flow in porous, permeable media. For example, the flow of a single-phase slightly compressible oil with a constant viscosity and compressibility the equations capture Darcy's law, the continuity condition and the equation of state and may be written as:

$$\nabla^2 p(x, t) = \frac{\varphi \mu c_t}{k} \frac{\partial p(x, t)}{\partial t} \qquad \text{Equation (9)}$$

where p represents fluid in the reservoir, x is a vector representing spatial position and t represents time. φ, μ, $c_t$, and k represent the physical and petrophysical properties of porosity, fluid viscosity, total combined rock and fluid compressibility, and permeability, respectively. $\nabla^2$ represents the spatial Laplacian operator.

Additional, and more complicated equations, such as the Peng-Robinson EoS (Equations (4)-(8), may be required when more than one fluid, or more than one phase, e.g., liquid and gas, are present in the reservoir. Further, when the physical and petrophysical properties of the rocks and fluids vary as a function of position the governing equations may not be solved analytically and must instead be discretized into a grid of cells or blocks. The governing equations must then be solved by one of a variety of numerical methods, such as, without limitation, explicit or implicit finite-difference methods, explicit or implicit finite element methods, or discrete Galerkin methods.

Figure 8:
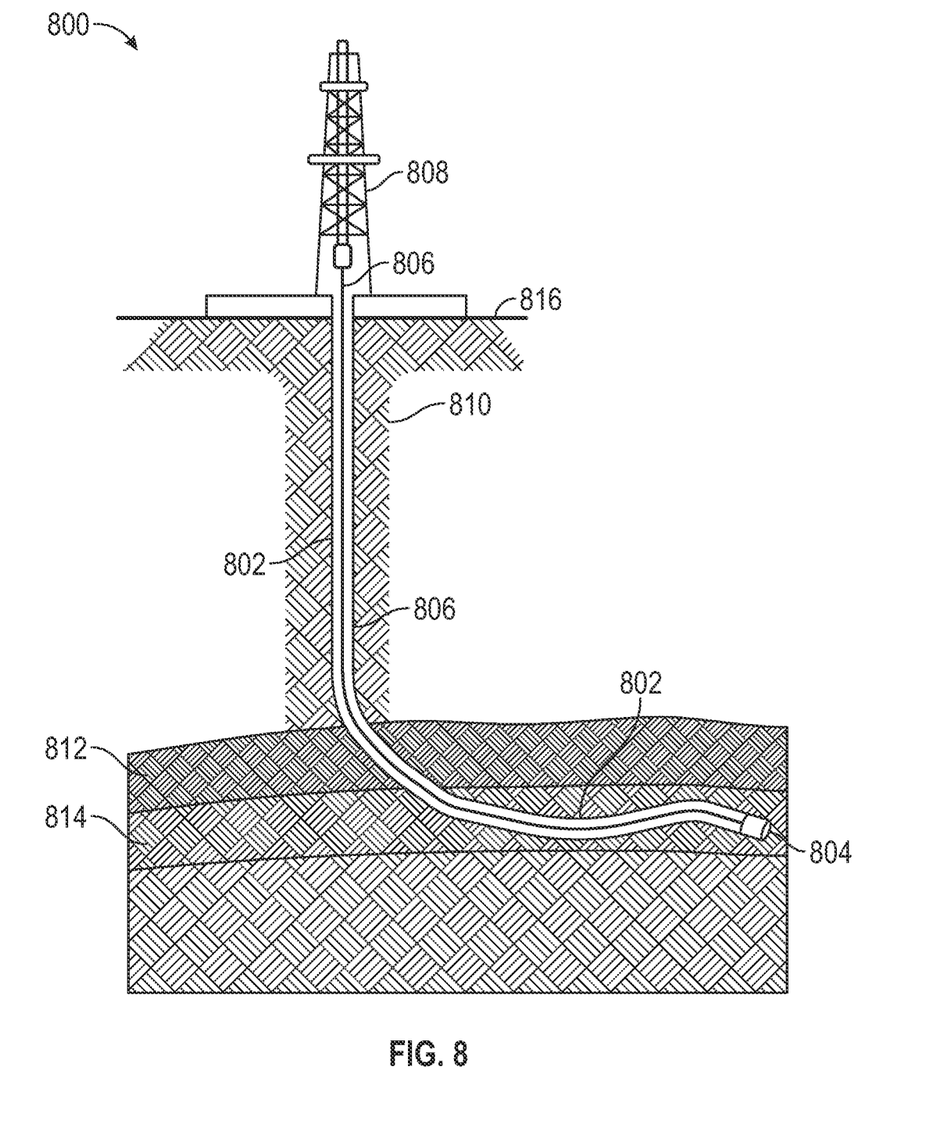
FIG. 8 shows a well system in accordance with one or more embodiments.

FIG. 8 illustrates a well system in accordance with one or more embodiments. As shown in FIG. 8, the well system (800) includes a well (802) that may be drilled by a drill bit (804) attached by a drill string (806) to a drill rig (808), which is located on the surface of the Earth (816). The well may traverse a plurality of overburden layers (810) and one or more cap-rock layers (812) to a hydrocarbon reservoir (814). In accordance with one or more embodiments, the critical desorption pressure and the EUR volume of gas may be used to plan and perform the curved well path. In particular, the proximity of adjacent wells to one another or the average spacing of wells may be determined based upon the critical desorption pressure and the EUR. Furthermore, the EUR may be used to plan the location and density of in-fill wellbores drilled between existing wellbores in later stages of reservoir development.

Although only a few example embodiments have been described in detail previously, those skilled in the art will readily appreciate that many modifications are possible in the example embodiments without materially departing from this disclosure. Accordingly, all such modifications are intended to be included within the scope of this disclosure as defined in the following claims. In the claims, any means-plus-function clauses are intended to cover the structures described as performing the recited function(s) and equivalents of those structures. Similarly, any step-plus-function clauses in the claims are intended to cover the acts described here as performing the recited function(s) and equivalents of those acts. It is the express intention of the applicant not to invoke 35 U.S.C. § 112(f) for any limitations of any of the claims, except for those in which the claim expressly uses the words "means for" or "step for" together with an associated function.

What is claimed is:

1. A method, comprising:
   obtaining, using a fluid sampling device, a plurality of fluid samples from an unconventional hydrocarbon reservoir,
   wherein the plurality of fluid samples comprises a first fluid sample at a first sample time, a second fluid sample at a second sample time, and a third fluid sample at a third sample time, and wherein the third sample time is later than the second sample time and the second sample time is later than the first sample time, and
   wherein each of the plurality of fluid samples comprises a gas sample;
   detecting, using a chemical composition analyzer, a measured chemical composition of each sample of the plurality of fluid samples;
   detecting, using an isotope ratio analyzer, measured isotope ratios of each sample of the plurality of fluid samples;
   detecting, using a pressure-volume-temperature analyzer, a measured pressure-volume-temperature behavior each sample of the plurality of fluid samples;
   using a computer processor:
      receiving the measured chemical composition, the measured isotope ratios, and the measured pressure-volume-temperature behavior of the first fluid sample,
      determining a measured relative volume of gas components from the measured chemical composition and the measured isotope ratios of the first fluid sample,
      determining an isotope ratio of gas components of the first fluid sample from the measured relative volume of gas components and the measured isotope ratios of the first fluid sample,
      determining an equation of state using the measured chemical composition, the measured pressure-volume-temperature behavior and the measured relative volume of gas components of the first fluid sample,
      receiving the measured chemical composition, the isotope ratios of gas, and the measured pressure-volume-temperature behavior of the second fluid sample and the third fluid sample,
      calibrating a parameter of the equation of state utilizing the measured chemical composition and the measured relative volume of gas components of the second fluid sample and the third fluid sample,
      predicting a predicted relative volume of gas components in a production flow based, at least in part, on the equation of state,
      determining, for each of the first fluid sample, the second fluid sample, and the third fluid sample, a desorption stage utilizing a temporal variation of isotope ratios of gas and a sequence of isotope ratios between methane, ethane and propane,
      determining a critical pressure and an extent of desorption utilizing a difference between the predicted relative volume of gas components from the measured relative volume of gas components,
      determining a quantity of produced desorbed gas under different pressures utilizing both the desorption stage and the difference between the predicted relative volume of gas components from the measured relative volume of gas components; and
   revising, using a reservoir simulator, an estimated ultimate recovery based, at least in part, on the determined desorption stage, the critical desorption pressure, and the quantity of produced desorbed gas.

2. The method of claim 1, further comprising planning and executing a production plan for the unconventional hydrocarbon reservoir based on the revised ultimate recovery.

3. The method of claim 2, wherein executing the production plan comprises injecting water into the unconventional hydrocarbon reservoir from wells around a periphery of the hydrocarbon reservoir.

4. The method of claim 1, wherein the first fluid sample comprises a fluid sample obtained from a fluid flow at a wellhead, a separator, or a gas oil separation plant.

5. The method of claim 1, wherein the equation of state is a Peng-Robinson equation of state, a Redlich-Kwong equation of state, or a derivation thereof.

6. A system, comprising:
   a fluid sampling device configured to obtain a plurality of fluid samples at a plurality of sample times from an unconventional hydrocarbon reservoir;
   a chemical composition analyzer configured to detect a measured chemical composition of each of the plurality of fluid samples;
   an isotope ratio analyzer configured to detect a measured value of an isotope ratio of each of the plurality of fluid samples;
   a pressure-volume-temperature analyzer configured to detect a measured pressure-volume-temperature behavior of each of the plurality of fluid samples; and
   a computer processor configured to:
      receive the measured chemical composition, the measured isotope ratios, and the measured pressure-volume-temperature behavior of the first fluid sample,
      determine a measured relative volume of gas components from the measured chemical composition and the measured isotope ratios of the first fluid sample,
      determining an isotope ratio of gas components of the first fluid sample from the measured relative volume of gas components and the measured isotope ratios of the first fluid sample,
      determine an equation of state using the measured chemical composition, the measured pressure-volume-temperature behavior and the measured relative volume of gas components of the first fluid sample,
      receive the measured chemical composition, the isotope ratios of gas, and the measured pressure-volume-temperature behavior of the second fluid sample and the third fluid sample,
      calibrate a parameter of the equation of state utilizing the measured chemical composition and the measured relative volume of gas components of the second fluid sample and the third fluid sample,
      predict a predicted relative volume of gas components in a production flow based, at least in part, on the equation of state,
      determine, for each of the first fluid sample, the second fluid sample, and the third fluid sample, a desorption stage utilizing a temporal variation of isotope ratios of gas and a sequence of isotope ratios between methane, ethane and propane;
      determine a critical pressure and an extent of desorption utilizing a difference between the predicted relative volume of gas components from the measured relative volume of gas components,
      determine a quantity of produced desorbed gas under different pressures utilizing both the desorption stage and the difference between the predicted relative volume of gas components from the measured relative volume of gas components; and a reservoir simulator, configure to revise an estimated ultimate recovery based, at least in part, on the determined desorption stage, the critical desorption pressure, and the quantity of produced desorbed gas.

7. The system of claim 6, further comprising a reservoir simulator to simulate hydrocarbon production from the unconventional hydrocarbon reservoir based on the estimated reservoir property.

8. The system of claim 6, wherein the estimated reservoir property comprises an estimated hydrocarbon production decline rate, an estimated ultimate recovery, a quantity of adsorbed gas in place, a quantity of desorbed gas in production from the unconventional hydrocarbon reservoir, a critical pressure of desorption, or a determined stage of desorption.

9. The system of claim 6, wherein detecting a first measured value of a fluid property comprises determining chemical composition, relative volume of gas components and isotope ratio of the gas components.

10. The system of claim 6, wherein the equation of state is a Peng-Robinson equation of state, a Redlich-Kwong equation of state, or a derivation thereof.

* * * * *